US012662444B2

(12) United States Patent
Kruse et al.

(10) Patent No.: US 12,662,444 B2
(45) Date of Patent: Jun. 23, 2026

(54) ALIPHATIC AMINE AND NITRILE SYNTHESIS THROUGH CATALYTIC CO HYDROGENATION IN THE PRESENCE OF AMMONIA

(71) Applicant: WASHINGTON STATE UNIVERSITY, Pullman, WA (US)

(72) Inventors: Norbert Kruse, Pullman, WA (US); Hafsa Karroum, Pullman, WA (US); Viacheslav Iablokov, Pullman, WA (US)

(73) Assignee: Washington State University, Pullman, WA (US)

( * ) Notice: Subject to any disclaimer, the term of this patent is extended or adjusted under 35 U.S.C. 154(b) by 807 days.

(21) Appl. No.: 17/997,769

(22) PCT Filed: Apr. 30, 2021

(86) PCT No.: PCT/US2021/030048
§ 371 (c)(1),
(2) Date: Nov. 2, 2022

(87) PCT Pub. No.: WO2021/225870
PCT Pub. Date: Nov. 11, 2021

(65) Prior Publication Data
US 2023/0144422 A1      May 11, 2023

Related U.S. Application Data

(60) Provisional application No. 63/021,431, filed on May 7, 2020.

(51) Int. Cl.
*C07C 209/26*      (2006.01)
*B01J 8/02*      (2006.01)
*B01J 23/889*      (2006.01)

(52) U.S. Cl.
CPC ............... *C07C 209/26* (2013.01); *B01J 8/02* (2013.01); *B01J 23/8892* (2013.01)

(58) Field of Classification Search
CPC ........ C07C 209/26; B01J 8/02; B01J 23/8892
See application file for complete search history.

(56) References Cited

U.S. PATENT DOCUMENTS 2,821,537 A      1/1958  Rottig
4,250,116 A      2/1981  Bartley
(Continued)

FOREIGN PATENT DOCUMENTS

WO      2018/029548 A1      2/2017

OTHER PUBLICATIONS

Nat. Commun. 2016, 7, 13058, pp. 1-6 (Xiang et al.) (Year: 2016).*
(Continued)

*Primary Examiner* — Amy C Bonaparte
*Assistant Examiner* — Derek Rhoades
(74) *Attorney, Agent, or Firm* — WCF IP

(57) ABSTRACT

A process for manufacturing aliphatic amines and nitriles by using the Fischer Tropsch synthesis (FTS), in the production of chain-lengthened hydrocarbons from CO and $H_2$ and their terminal nitrogen functionalization using ammonia. The method can include activating a catalyst with a feed gas, wherein the feed gas comprises $H_2$/CO mixtures; providing a temperature between 180° C. and 300° C. under a pressure between 1 bar to 25 bar; wherein the nitrogenates include at least one aliphatic amine and/or nitrile; and setting or adjusting the $H_2$/CO ratio to selectively synthesize amines and/or nitriles over other nitrogen containing compounds.

26 Claims, 9 Drawing Sheets

(56)                    References Cited

U.S. PATENT DOCUMENTS

| 5,585,316 | A | * | 12/1996 | Nay et al. ............... | B01J 20/30 |
| | | | | | 502/50 |
| 2005/0154069 | A1 | | 7/2005 | Inga | |
| 2005/0182150 | A1 | | 8/2005 | Bamborough | |
| 2011/0092728 | A1 | | 4/2011 | Claeys | |

OTHER PUBLICATIONS

J. Phys. Chem. B 2005, 109, 2350-2359 (Frennet et al.) (Year: 2005).*
Practical Process & Research Development, 2000, pp. 168-169 and 171 (Anderson) (Year: 2000).*

\* cited by examiner

| Ar / H₂ ➔ He / H₂ / CO | Build Up | Ar / H₂ ➔ He / H₂ / CO / NH₃ |
|---|---|---|
| 25ml / 5mL ➔ 20m L/ 5mL / 5mL | Co₄ZrOₓ | 25ml / 5mL ➔ 10m L/ 5mL / 5mL/ 10 mL |

| Time Appearance | CH₄ | CO₂ | CO | H₂O | NH₃ |
|---|---|---|---|---|---|
| No NH₃ | 2 sec | 32 sec | 22 sec | 160 sec | / |
| With NH₃ | 9 sec | 19 sec | 16 sec | 32 sec | 28 sec |

| Co | | | | | | | |
|---|---|---|---|---|---|---|---|
| No NH₃ | 17 % | 21 % | 41 % | 38 % | <1% | / | 15 % |
| With NH₃ | 11 % | 3 % | 12 % | 77 % | / | 8 % | 8 % |
| Co₄Nh₃ | | | | | | | |
| No NH₃ | 17 % | 10 % | 31 % | 59 % | <1% | / | 24 % |
| With NH₃ | 77 % | 4 % | 14 % | 77 % | / | 6 % | 13 % |
| Co₄ZrOₓ | | | | | | | |
| No NH₃ | 15 % | 9 % | 27 % | 64 % | / | / | 27 % |
| With NH₃ | 58 % | 4 % | 13 % | 79 % | / | 4 % | 13 % |

ALIPHATIC AMINE AND NITRILE SYNTHESIS THROUGH CATALYTIC CO HYDROGENATION IN THE PRESENCE OF AMMONIA

CROSS REFERENCE TO RELATED APPLICATIONS

This application claims priority to U.S. Provisional Application 63/021,431 filed May 7, 2020, and the complete contents thereof is herein incorporated by reference.

FIELD OF INVENTION

The embodiments herein relate to synthesis of desired nitrogen containing hydrocarbons and more particularly, to the synthesis of desired nitrogen containing hydrocarbons, such as, but not limited to, aliphatic amines and nitriles using catalytic CO hydrogenation and ammonia as an agent to provide terminal nitrogen functionalization.

BACKGROUND OF THE INVENTION

The global demand for amines and nitriles is growing rapidly ($2.9 billion by 2025). The market of high-quality surfactants and emulsifiers is one of the main drivers for this development. In addition, due to their chemical structure and propensity to replace an electron, amines are most frequently used in the pharmaceutical industries for a wide range of therapeutics (e.g., pain killers, decongestants, psychedelic drugs, sedatives, etc.). Amines are generally categorized into three subcategories; primary, secondary and tertiary amines, depending on the number of substituents on nitrogen. Amines are further divided into aliphatic, aromatic and heterocyclic amines. Among these categories, aliphatic amines are defined as amines with only H and alkyl substituent. Traditionally, aliphatic amines are synthesized in multi-step processes that treat feeds of alcohols, aldehydes, olefins, nitriles or carboxylic acids with a nitrogen source such as ammonia. Such ammonia-based synthesis processes of amines lead to the formation of mixtures of primary, secondary, and tertiary amines along with the quaternary salts. This is because the primary amine product in the reaction may rapidly react to form the secondary amine, which in turn will again react to form the tertiary amine, which also possibly further reacts to form the quaternary salt.

Current methods employed to make aliphatic amines are hydroamination, reductive amination, amination of olefins and hydrogenation of nitriles. On the other hand, nitriles are produced by either ammoxidation or hydrocyanation using alkenes as target molecules. However, the major drawbacks of such traditional synthesis routes are their use of expensive reagents, multi-step processes, formation of toxic by-products and poor selectivity to primary amines and nitriles.

Early work on nitrogen containing hydrocarbons using a modified Fischer-Tropsch synthesis, as known by those of ordinary skill in the art, (e.g., Ruhrchemie, 1949), entailed adding small amounts of ammonia (0.5 to 5%) to synthesis gas (CO+H₂) over an iron (Fe)-based catalyst system. More recently, Claeys et al. showed that the addition of ammonia (up to 20 vol %) to a syngas feed significantly decreases the activity of supported or unsupported iron or cobalt catalysts in a slurry phase reactor. In particular, background information on such a method is described and claimed in, U.S. Pat. No. 7,339,521, entitled, "PROCESS FOR THE PRODUCTION OF NITROGEN OR PHOSPHOROUS CONTAINING COMPOUNDS FROM SYNTHESIS GAS," issued Aug. 20, 2013, to Claeys et al., incorporated herein by reference, including the following, "[a] process is described for the production of one or more of linear nitriles, amides and formamides which includes reacting a nitrogen containing compound, such as ammonia or NO$_N$, and a synthesis gas over a catalyst at a temperature of between 160° C. and 400° C. and a pressure of between 1 bar and 50 bar. A further process for the production of one or more of linear phosphorous containing compounds is also described, which includes reacting a phosphorous containing compound, such as a phosphine, and a synthesis gas over a catalyst at a temperature of between 160° C. and 400° C. and a pressure of between 1 bar and 50 bar. A supported cobalt, iron, ruthenium or rhodium catalyst or an unsupported (bulk) promoted iron catalyst, modified with a promoter is used." Of note, the production process of Claeys et al. describes oxygenates such as alcohols, aldehydes and acids to react with ammonia to form the desired products and even favors additional supply of oxygenates during the reaction. Moreover, Claeys et al. do not disclose or suggest the use of an active phase of the catalysts that enables the beneficial production of the resultant hydrocarbons, as to be shown herein.

In another work, Fisher, N. et al., *Catal. Commun.* 87, 14-17 (2016), entitled: "Acetonitrile via CO hydrogenation in the presence of NH₃", reports selectivity towards acetonitrile over an FeRh catalyst that also occurs at the expense of oxygenates, mostly ethanol, which was formed in the absence of ammonia. Such a disclosure includes the following "[w]e are presenting the use of an alumina supported FeRh alloy catalyst for the formation of nitrogen containing compounds via the CO hydrogenation in the presence of ammonia. In contrast to previous studies on either similar catalyst systems or on an iron-based catalyst, the prepared FeRh material displays a high selectivity to a single nitrogen-containing compound, acetonitrile. The formation of acetonitrile occurs at the expense of oxygenates, mostly ethanol, which form in the absence of ammonia." However, it is to be appreciated that high-pressure synthesis of long-chain amines and nitriles over an active phase of the catalyst in conjunction with a suitable metal-oxide and alkali promoter in a plug flow reactor is still not utilized and has never been provided in the industry despite the need in the art.

In essence, reported work on the synthesis of aliphatic amines and nitriles from the CO hydrogenation in the presence of ammonia lack at providing both a process to properly activate the catalyst and a process to tune the reaction in order to optimize the selectivity toward nitrogen-containing compounds such as aliphatic amines and nitriles.

Accordingly, a need exists for a selective "one-step one-pot" synthesis to provide for a high production of functionalized hydrocarbons, such as, aliphatic amines and nitriles using activated catalysts of Co (e.g., as Co₂C) promoted with metal oxides and alkali, wherein catalytic CO hydrogenation is used as a vehicle to produce hydrocarbon chain lengthening and ammonia as an agent to provide terminal nitrogen functionalization. The embodiments herein address such a need.

SUMMARY OF THE INVENTION

The embodiments herein, as even further detailed in the specific description discussed below, exploit the beneficial novel process disclosed herein for the manufacture of aliphatic fatty amines by combining the Fischer Tropsch synthesis (FTS), which provides for production of chain-lengthened hydrocarbons from CO and H₂ and their terminal nitrogen functionalization using ammonia. In particular, chain-lengthened hydrocarbons can be functionalized with oxygen to provide either terminal alcohols or aldehydes with high selectivity of up to 90% in a "one step—one pot" approach using Cu- and Mn-promoted Co-catalysts, wherein a CO insertion mechanism is in operation for hydrocarbon chain lengthening.

One aspect of the disclosure includes a process of aliphatic terminal amines and/or nitriles formation in a catalyst-based reaction in which the amines and nitriles are produced completely independent of a non-catalytic reaction between ammonia and oxygenates in a gas phase. Such synthesis mechanism disclosed herein ensures selectivity of a primary amine over a secondary amine. In some embodiments, the amines and nitriles are formulated in a plurality of types of reactors. In preferred embodiments, the amines and nitriles are formulated in a fixed-bed reactor.

Another aspect disclosed herein includes a reactor-based hydrogenation process for producing nitrogen containing hydrocarbons, comprising reacting one or more catalysts with a synthesis gas comprising carbon monoxide (CO) and hydrogen ($H_2$) under Fischer-Tropsch reaction conditions in the presence of ammonia to produce at least one aliphatic amine and/or nitrile, and adjusting a ratio of $H_2$ to CO to selectively form the at least one aliphatic amine and/or nitrile.

Another aspect disclosed herein includes a method to catalytically synthesize chain-lengthened hydrocarbons with terminal nitrogen functionalization, including: activating a catalyst with a feed gas, wherein the feed gas comprises $H_2$/CO mixtures; adding ammonia to the $H_2$/CO reaction mixtures, wherein the activating step includes performing the reaction at a first low $H_2$/CO ratio of 0.3 up to 0.5 for 24 hours in the presence of a promoter in order to generate $Co_2C$, which is the active phase so as to form nitrogen-containing compounds; and providing a temperature between 180° C. and 300° C. under a pressure between 1 bar to 25 bar; wherein the nitrogenates include at least one aliphatic amine and/or nitrile.

The disclosure also provides a method of setting or adjusting the $H_2$/CO ratio to selectively form one class of nitrogen containing compound over the others while maintaining other reaction conditions and components the same. The $H_2$/CO ratio may be adjusted during the reaction, once the one or more catalysts are reconstructed into an active phase in the reaction. Another aspect of the disclosure includes a method of suppressing the formation of other nitrogen containing compounds (e.g., amides and formamides) in presence of ammonia as well as alkanes and alcohols in a reaction disclosed herein.

DETAILED DESCRIPTION OF THE INVENTION

Figure 1:
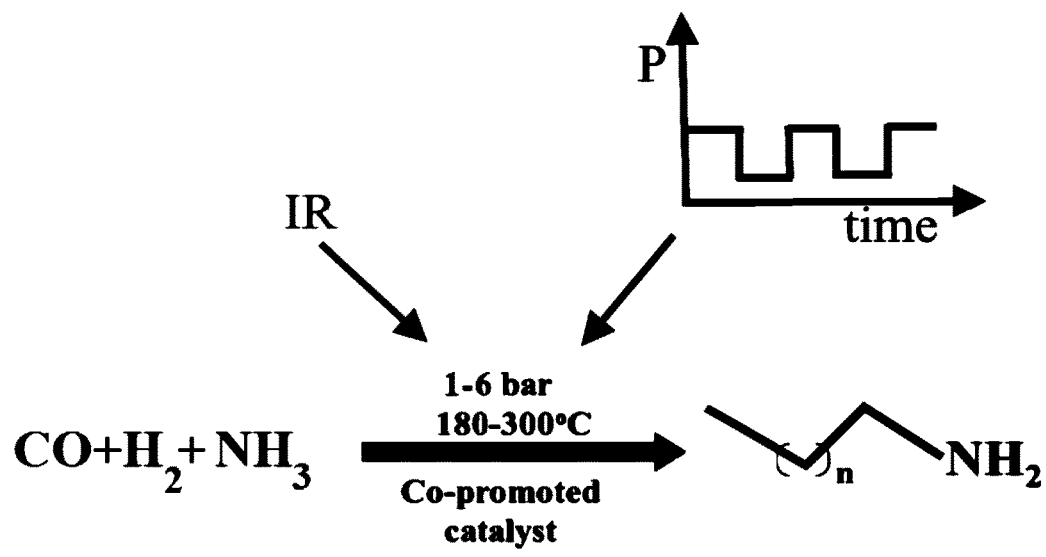
FIG. 1 shows an exemplary scheme of aliphatic amine synthesis by IR (DRIFTS) and partial pressure jumps (Chemical Transient Kinetics, CTK).

In the description of the invention herein, it is understood that a word appearing in the singular encompasses its plural counterpart, and a word appearing in the plural encompasses its singular counterpart, unless implicitly or explicitly understood or stated otherwise. Furthermore, it is understood that for any given component or embodiment described herein, any of the possible candidates or alternatives listed for that component may generally be used individually or in combination with one another, unless implicitly or explicitly understood or stated otherwise. Moreover, it is to be appreciated that the figures, as shown herein, are not necessarily drawn to scale, wherein some of the elements may be drawn merely for clarity of the invention. Also, reference numerals may be repeated among the various figures to show corresponding or analogous elements. Additionally, it is understood that any list of such candidates or alternatives is merely illustrative, not limiting, unless implicitly or explicitly understood or stated otherwise. In addition, unless otherwise indicated, numbers expressing quantities of ingredients, constituents, reaction conditions and so forth used in the specification and claims are to be understood as being modified by the term "about."

Accordingly, unless indicated to the contrary, the numerical parameters set forth in the specification and attached claims are approximations that may vary depending upon the desired properties sought to be obtained by the subject matter presented herein. At the very least, and not as an attempt to limit the application of the doctrine of equivalents to the scope of the claims, each numerical parameter should at least be construed in light of the number of reported significant digits and by applying ordinary rounding techniques. Notwithstanding that the numerical ranges and parameters setting forth the broad scope of the subject matter presented herein are approximations, the numerical values set forth in the specific examples are reported as precisely as possible. Any numerical values, however, inherently contain certain errors necessarily resulting from the standard deviation found in their respective testing measurements.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

GENERAL DESCRIPTION

It is to be appreciated that while (migratory) CO insertion is deemed a guiding mechanistic concept in hydroformylation (production of aldehydes by homogeneous CO hydrogenation in the presence of terminal olefins using ligand-substituted Co, Rh-carbonyls as a catalyst), it is much less so in heterogeneous catalysis. In an unexpected and surprising result, it is disclosed that adding ammonia to $H_2$/CO reaction mixtures, and using the same catalysts that are active in oxygenate production from pure syngas, "transforms" the analytic data from those of alcohols to those of amines, even in the absence of additionally supplied oxygenates in the reaction.

The embodiments herein thus disclose a process for manufacturing of desired hydrocarbons, such as, but not limited to, aliphatic amines and nitriles by combining the Fischer Tropsch synthesis (FTS), which includes the production of chain-lengthened hydrocarbons from CO and $H_2$, and their terminal nitrogen functionalization using ammonia.

The "Fischer-Tropsch synthesis (FTS) condition" described herein refers to a collection of chemical reaction conditions that converts a mixture of carbon monoxide and hydrogen into liquid hydrocarbons in the presence of metal catalysts, typically at temperatures of 150-300° C. and at pressures of 1-30 bar. Additional equipment, design parameters and conditions that are required for the FTS reactions are known in the art and readily apparent from U.S. Pat. Nos. 4,585,798; 5,585,316; 6,753,351; and 8,614,158, all of which are incorporated by reference in their entirety as part of the disclosure herein.

CO hydrogenation in the presence of ammonia may be conducted over a catalyst, such as a cobalt catalyst promoted with alkali and metal oxides, such as manganese oxide, zirconium oxide, lanthanum oxide, titanium oxide and cerium oxide. The reaction may be performed in a plug flow reactor or a fixed bed reactor in which a catalyst reacts with the feed/synthesis gas at a temperature between 150° C. to 300° C., e.g. 220° C. to 280° C. and under a pressure between 1 to 30 bar, e.g. 5-20 bar.

The reaction can be tuned to favor one class of nitrogen containing compounds over others by adjusting the $H_2$/CO ratio. The ratio of hydrogen to carbon monoxide can be varied from 0.3:1 to 7:1. Nitriles are formed at low $H_2$/CO ratio (i.e. $H_2$/CO=0.5:1), but not exclusively, while amines are favored at moderate $H_2$/CO ratios (i.e. $H_2$/CO=3:1).

The reaction often may first be performed at low $H_2$/CO ratio in order to transform metallic Co into $Co_2C$, which is responsible for the formation of functionalized hydrocarbons such as amines, nitriles, alcohols and aldehydes.

Ammonia can either be added in the feed gas at the onset of the reaction or after 24 h time-on-stream of the Fischer-Tropsch reaction. Both scenarios lead to the formation of nitrogen-containing compounds and to the formation of cobalt carbide.

The example embodiments provide for a process that inhibits the formation of methane, aliphatic alkanes and oxygenates such as alcohols and aldehydes. The process also increases the selectivity of olefins at the expense of all other products.

Moreover, the example embodiments provide for a process that is completely reversible once ammonia is removed from the feed gas, i.e. the initial Fischer-Tropsch catalytic performance, whatever $H_2$/CO ratio, is reproduced once ammonia is removed from the reactant feed.

SPECIFIC DESCRIPTION

FIG. 1 shows an exemplary scheme of the present invention for aliphatic amine synthesis using Chemical Transient Kinetics (CTK) with Diffuse Reflectance Infrared Fourier Transform Spectroscopy (DRIFTS) and partial pressure jumps, wherein high-pressure synthesis may involve pressures up to 25 bar while CTK and IR analyses are often up to 6 bar. CTK was often employed along with DRIFTS as a means to monitor product formation in a time-resolved manner and to determine the chemical nature of the adsorbed intermediates via a rigorous vibrational analysis.

Accordingly, catalysts were prepared, as disclosed herein, via oxalate precipitation. As known to those of ordinary skill in the art, metal oxalates are organic precursors in which the oxalate acts as a double-chelating ligand between metal atoms. Polymer strings are formed which resemble Metal-Organic-Framework (MOF) structures. To produce active catalysts, oxalate precursors are thermally decomposed in a temperature-programmed manner and in the presence of hydrogen. During the thermal decomposition of the metal oxalate, the oxalate ligands are stripped off as either CO or $CO_2$ to produce small particles of the active catalyst. No generic support material is needed when using such an oxalate route. If the thermal decomposition of the oxalate framework structure leads to pure metal(s)—in this case the only decomposition product is $CO_2$—the specific surface is of several $m^2$/g. However, if the decomposition leads to both metal and metal oxide phases, the specific surface area can become large (>100 $m^2$/gr). Metal oxide particles formed that way may serve as dispersant (support) and/or as a promoter since they may not be chemically inert.

The beneficial aspects of the embodiments herein include using different metals that are co-precipitated into neighboring positions of the same MOF structure at the instant of precipitation. As a result, "cobalt-manganese" and "cobalt-zirconium" have been prepared. It is to be noted that alkali is co-precipitated in the MOF structure by entrainment and solubility effects using mixtures of different solvents.

Mn-oxide-promoted cobalt and Zr-oxide-promoted cobalt catalysts were prepared for the synthesis of aliphatic amines and nitriles from $CO/H_2/NH_3$ feeds. The choice of the metal oxides, as disclosed herein, is based on suitability of such catalysts for long-chain oxygenates synthesis during the Fischer-Tropsch reaction. Accordingly, such catalysts are likewise suited for chain-lengthened amines and nitriles. Successful catalyst formulations (in terms of steady-state activity and selectivity) were subjected to a rigorous kinetic and mechanistic analysis to provide the foundational understanding of the relevant reaction networks. A strategic approach to enable the embodiments herein, included in-operando type Chemical Transient Kinetics (CTK).

Amines and nitriles were synthesized from promoted and unpromoted cobalt catalyst at a pressure varying from atmospheric pressure to 25 bar. Best catalytic performances were obtained at 20 bar over $Co_4Mn_1K_{0.1}$ (indices stand for atomic amounts).

Different alkali metals were used in varying amounts. While all catalysts promoted with alkali form nitrogen containing compounds, only catalysts promoted with Li and Na showed the formation of a white solid powder, which IR analysis revealed to be ammonium carbonate. The white solid powder was not present when the gas feed lines were heated to 70° C.

All catalysts were activated in-situ by a hydrogen-assisted thermal decomposition. Then, catalytic tests started by running the reaction at low $H_2/CO$ ratio (e.g., a $H_2/CO=0.3$-0.5). This step is beneficial for the formation of nitrogen-containing compounds. Indeed, this step reconstructs the Co catalyst into cobalt carbide; this latter is the active key phase for the formation of functionalized hydrocarbons through CO hydrogenation. Ammonia can either be added to the feed gas before starting the FT reaction or when the FT reaction reaches its steady-state (24 hours on stream), wherein both scenarios lead to the formation of cobalt carbide. In some embodiments, 20-30 hours on stream time may be needed for the formation of active phase catalysts (e.g., cobalt carbide).

Once the catalyst is reconstructed into an active phase of the catalyst (containing e.g., cobalt carbide) the $H_2/CO$ can be adjusted in order to selectively form one class of nitrogen containing-compound over the others. For example, nitriles are favored at low $H_2/CO$ ratio (a $H_2/CO$ from 0.3:1 to 0.5:1) while amines are favored at moderate $H_2/CO$ ratio (a $H_2/CO$ from 2:1 up to 3:1).

The traditional Fischer-Tropsch product spectra return as soon as ammonia is removed from the feed stock. The reversibility of the reaction indicates that ammonia interacts with the surface of the catalyst without reconstructing the bulk of the catalyst. XRD analysis shows that the composition of the bulk of the catalyst is not affected by ammonia, wherein $Co_2C$ remains the active phase. Ammonia rapidly inhibits the formation of methane, alkanes and ISO products, while the selectivity for olefin production increases significantly.

Product distributions have been evaluated in terms of chain lengthening probabilities in the presence and absence of ammonia in the feed gas. Anderson-Schulz-Flory (ASF) plots show that ammonia, independent of the $H_2/CO$ ratio, drastically disturbs the linearity of the alkanes $C_4^+$ ASF while increasing the chain lengthening probabilities of alkenes and nitrogen-containing compounds.

Chemical Transient Kinetics has been used to provide microkinetic information. Accordingly, $NH_3$ as co-feed of syngas reduces methane as well as alkanes but increases carbon dioxide formation at the same time.

Example 1

Table 1 below shows first catalytic performance data for high-pressure CO-hydrogenation in the absence and presence of ammonia (15% of the total feed). Conversion and selectivity refer to 12 h time-on-stream.

TABLE 1

| | | |
|---|---|---|
| Co$_4$Mn$_1$K$_{0.1}$ 260° C./17 bar/SiO$_2$ H$_2$/CO = 3 | | |
| | FT | 15 vol. % NH$_3$ |
| % CO$_2$ | 35 | 25 |
| % CH$_4$ | 17 | 19 |
| n % Alkanes | 18 | 24 |
| % Alkenes | 32 | 32 |
| % R—OH | 33 | / |
| % R═O | 0 | / |
| % R—NH$_2$ | / | 25 |
| % R≡N | / | 0 |
| CO conversion | 56 | 31 |

First encouraging results were obtained for $Co_4Mn_1K_{0.1}$ catalysts (indices indicating metal atomic amounts) dispersed on silica. A total pressure of 17 bar has been established in these measurements using a fixed-bed flow reactor with heated gas lines (note that the molecule liquefies at about 8 bar and 300 K). As can be seen, alcohols, despite the CO conversion at 260° C. decreasing from 56% to 31%, formed with a selectivity of 33% (ex-$CO_2$) under typical Fischer Tropsch synthesis conditions while they are absent in the presence of ammonia. Instead, 25% (ex-$CO_2$) of chain lengthened amines are produced. Products up to $C_5$ were detected. Additional results with a pressure ratio of $H_2/CO=0.5:1$ show aldehyde rather than alcohol formation. Surprisingly and unexpectedly, these aldehydes are being quantitatively replaced by nitriles when running the synthesis in the presence of ammonia.

Experiments/Results

Figure 2:
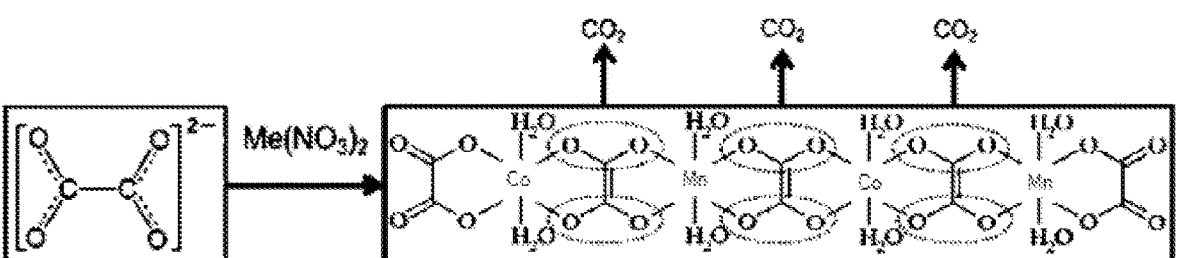
FIG. 2 shows oxalate co-precipitation to form a Metal Organic Framework.

Catalysts were prepared according to the oxalate precipitation method. Using metal salts (nitrates by preference) in aqueous solution, the precipitation with oxalic acid provides a polymeric metal organic framework (MOF). FIG. 2 shows oxalate co-precipitation to form a Metal Organic Framework. In particular, FIG. 2 shows oxalate anions operating as chelating ligands linking metal cations. Mild heating causes collapse of the polymer and formation of nanosized mixed-metal particles or (as indicated for Co—Mn system) phase separation into nanosized metal and metal-oxide particles. One of the benefits of catalyst preparation disclosed herein via oxalates is that different metals co-precipitate into neighboring positions of the same MOF structure at the instant of precipitation. This way, binary and ternary oxalates are prepared.

It is noted that alkali oxalates are water-soluble and have to be co-precipitated using "solubility effects". Rather than triggering oxalate co-precipitation from nitrate precursors in pure water, acetone-water mixtures are used instead. Precipitated oxalates either serve directly as precursors in the absence of a generic support or are being dispersed onto silica by impregnation methods involving suitable solvents. In some embodiments, the solvent may be an organic solvent, such as acetone, methanol, higher alcohols, hexane, benzene, and the like. The impregnation may be incipient wetness impregnation. Further, the impregnation may include slurrying the support into the solution containing the precursor compound. Preferably, the one or more catalysts are prepared via the oxalate precipitation method described herein. Alternatively, in some embodiments, other CoMn catalyst preparation methods known in the art (e.g. hot-injection of $Co_2(CO)_8$ and thermal decomposition of Mn-oxalate to generate Co particles on $MnO_x$) may also be used.

Metal-oxalate precursors, either $SiO_2$-supported or not, are activated by hydrogen-assisted Temperature Programmed Decomposition (TPDec). Suitable cobalt-containing precursor compounds include, for example, cobalt oxalate, hydrated cobalt nitrate, cobalt carbonyl, cobalt oxide, cobalt acetate, cobalt acetylacetonate, cobalt benzyolacetonate, and the like. While Co oxalate decomposition leads to pure Co, Mn does not reach the metallic state. Instead, it retains some of the oxygen of the oxalate framework and forms Mn-oxides, predominantly in form of $Mn_5O_8$. The occurrence of metal oxides is evaluated by measuring the relative amounts of liberated CO and $CO_2$ molecules. An intimate mixing of Co metal and Mn-oxides is obtained.

Mn-oxides ($MnO_x$) and Zr-oxide ($ZrO_x$) play the role of both a dispersant and promotor while alkali is anticipated to mainly act as a promoter. Additionally, other oxides or metals such as Ti, Mg, Cr, Ca, Si, Al, Cu or combinations thereof may be used as a dispersant and/or promoter. Note that despite the absence of a generic support in this preparation route, catalysts prepared via oxalates provide significant long-term stability. In preliminary tests it was observed that $SiO_2$ supported $Co_4Mn_1K_{0.1}$ catalysts yet may have beneficial aspects over non-supported ones. The relative amounts and chemical nature of alkali in $Co/MnO_x$-based and $Co/ZrO_x$-based catalysts have an impact. Accordingly, besides K, promoter action of Li, Na and Cs in both supported and unsupported catalysts is observed.

Catalysts activated by $H_2$-TPDec are subjected to a physico-chemical characterization using microscopic and spectroscopic methods. The specific surface areas of the entire catalyst and the metallic part of it are determined from BET isotherms and $H_2$-$D_2$ exchange measurements, respectively. The $H_2$-$D_2$ exchange method allows metal surface atoms to be titrated by following HD formation. Catalysts are also examined by (HR)TEM to provide independent information on particle sizes and morphologies. X-ray Diffraction (XRD) studies inform about bulk phase compositions. Activated catalyst formulations are subjected to aliphatic amine and nitrile synthesis in a fixed-bed flow reactor at variable total and partial pressures of the reactants. Steady-state reactant conversions are measured along with product selectivity at various temperatures up to 300° C. Anderson-Schulz-Flory chain lengthening probabilities are determined for each product class. On-line quadrupole mass spectrometry (MS) and gas chromatography (GC), either combined in GCMS or separately, are available as analytical tools.

Relevant Co-based catalyst formulations are prepared via oxalate-mediated MOF structures. MOF catalyst precursors containing multiple metals are activated by $H_2$-assisted TPDec. The resulting $Co$-$MeO_x$ structures are fully characterized for their physico-chemical properties. Steady-state catalytic tests demonstrate the catalytic performance and provide information on the macrokinetics.

Example 2

Aliphatic Amines and nitriles synthesis over most favorable $Co/MeO_x$ catalyst formulations are subjected to a detailed microkinetic and mechanistic investigation using CTK. Mainly unsupported catalysts are studied (the dilution effect by $SiO_2$ decreases the signal response sensitivity) using $CO/H_2/NH_3$ gas feeds with an upper total pressure limit of 6 bar (amination in the variable-pressure, fixed-bed flow reactor has already been seen to occur at this pressure). The experiments are performed in a CTK-adapted fixed-bed reactor with close-to-CSTR behavior. The same reactor allows for physico-chemical characterization using BET and dynamic $H_2$-$D_2$ exchange, so this unique conceptional design avoids any sample transfer effects between characterization devices and dedicated reaction vessels.

Figure 3:
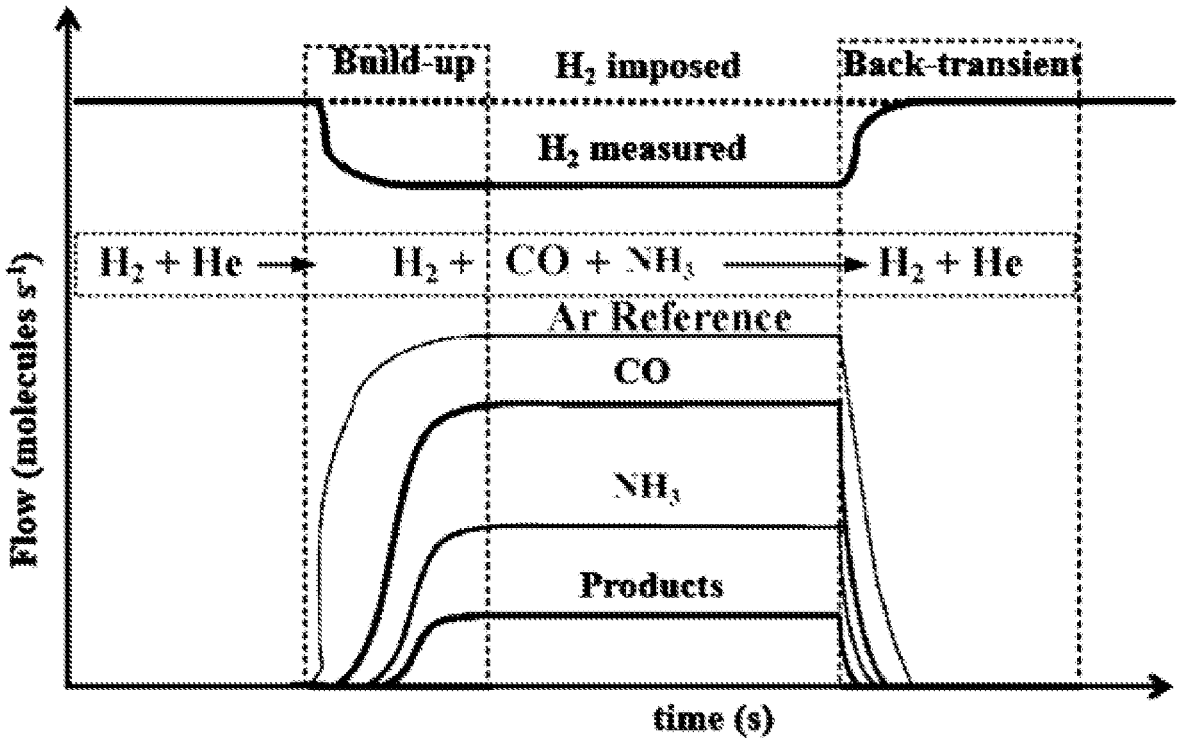
FIG. 3 shows CTK time-dependent measurements of embodiments of the present invention.

CTK studies, as described in more detail below, were performed by switching gas feed compositions abruptly from non-reactive to reactive ones and vice versa. FIG. 3, in particular, shows the principle of operation via illustrated CTK time-dependent measurements, wherein abrupt changes of gas phase compositions provide kinetic information on the formation of products. Most importantly, the time-dependent formation of product molecules after switching from $H_2$ gas (in the presence of a reference gas like He) to $CO/H_2/NH_3$ feeds (using Ar balance as reference gas) is followed. Since a polymerization type of hydrocarbon chain lengthening is in operation, products with increasing number of carbon atoms show up sequentially.

Under calibrated flow conditions, quantitation becomes possible. It is to be noted that measurements can also be performed by repetitive feed pulsing. Furthermore, possible delays in reactant appearance at the reactor exit are evaluated. Ultimately, the delay time analysis of products and reactants allows to determine at which point in time CO insertion as chain lengthening step takes place relative to N-functionalization. Accordingly, similar to the chain lengthening mechanism leading to oxygenates via repetitive CO insertion into the O—R bond of alkoxy, it is assumed that CO is inserted into the N—H bond of adsorbed amine. Switching back from steady-state conditions to $H_2$ adsorption conditions, as shown in FIG. 3, is informative of characteristic decay times. Because of the complexity of gas mixtures and reaction networks, quadrupole mass spectrometry can be beneficially combined along with "multiple-loop" gas chromatography as analytical device for measuring time dependent product formation.

Because the flow reactor in CTK is being operated under conditions of vanishing concentration gradients in the reactor, a mass balance is set up and solved to trace the atomic amounts of adsorbing carbon, oxygen, hydrogen and nitrogen from the instant of switching to build-up and, vice versa, from steady-state to scavenging (back-transient). The quantitative assessment of atomic amounts provides important ingredients to develop a mechanism for hydrocarbon skeleton growth on the one hand and O, N-terminal functionalization on the other.

The detailed microkinetic/vibrational analysis shows that i) CO as the inserting monomer would appear responsible for hydrocarbon chain growth from mixed $H_2/CO/NH_3$ feeds and provide a ii) mechanism to form aliphatic amines and nitriles with regioselective terminal N-functionalization. The information received from this insight guides the targeted design of catalysts for aliphatic amine and nitrile synthesis.

Materials and Methods

A. Catalyst Preparation $Co_4Mn_1K_{0.1}$ catalyst was prepared via oxalate co-precipitation. To do so, a solution of both $Co(NO_3)_2$ $6H_2O$ and $Mn(NO_3)_2$ $4H_2O$ in acetone (100 ml), an aqueous solution of $KNO_3$ (5 ml), and an acetone solution of $H_2C_2O_4$ $2H_2O$ (150 ml) were prepared in three separated beakers. Then the mixed acetone solution of $Co(NO_3)_2$ $6H_2O$ and $Mn(NO_3)_2$ $4H_2O$ together with the aqueous solution of $KNO_3$ were added fast and simultaneously, under vigorous stirring, to the solution of $H_2C_2O_4$ $2H_2O$. Stirring was kept for at least 5 min until the color of the precipitates appeared homogeneous. Then the slurries were kept overnight for aging. After removal of the supernatant acetone, the precipitate was centrifuged and dried overnight at 110° C.

B. Catalytic Testing

High-pressure catalytic tests were performed in a fixed-bed flow reactor consisting of a quartz tubule (Finner ¼ 7 mm) inserted into a stainless-steel housing. A condenser along with a gas-liquid separator was mounted at the reactor outlet in order to collect the liquid products of the reaction. Prior to catalytic tests, the oxalate precursor was subjected to an in-situ thermal decomposition at 390° C. for 1 h under $H_2$ at atmospheric pressure.

After the oxalate decomposition, the amount of activated catalyst was about 0.3 g. The reactor was subsequently cooled to a temperature below 100° C. in flowing hydrogen before adding CO to produce a syngas feed with the desired $H_2/CO$ ratio; the total typical flow rate was 40 mL/min. Metal carbonyls (mainly $Ni(CO)_4$) were removed by passing the CO feed through a heated zeolite 4A trap before introduction into the reactor. Once the system was pressurized to 17 bar, the temperature was raised using a low heating rate of 1° C./min up to 260° C. The reaction was kept overnight under these conditions. 7 ml/min of ammonia were then introduced into the reactor, corresponding to 15% of the total inlet feed volume. Catalytic activities and products selectivity were determined after stabilization for at least 12 hours and measured by online GC-MS (Agilent 7890A GC/5975 MS).

C. Catalyst's Bulk Characterization

X-ray diffraction (XRD) was performed with a Cu Kα source using a Rigaku Miniflex-600 X-ray diffractometer operating at 40 mA and 35 kV in the continuous-scan mode. with steps of 1 degree/min in a wide 2θ angle range from 20° to 80°.

D. Surface Analysis

XPS experiments were performed in an AXIS Nova photoelectron spectrometer (Kratos Analytical, Manchester/UK) at a base pressure of <1·10-8 mbar, using Al Kα monochromatic radiation (1486.6 eV), monochromatized by a 500 mm Rowland circle geometry at an operating source power of 15 kV×10 mA (=150 W). Photoelectron spectra were acquired with a hemispherical energy analyzer in a constant pass energy mode of EP=160 eV for survey spectra and EP=10 eV for core-level spectra. Measurements were done in slot mode, giving a spot of analysis with size 300 μm×700 μm. For a detailed analysis of the surface chemical state of the catalyst, the core-level spectra with subtracted background were decomposed into their components by a non-linear least squares curve-fitting procedure with mixed Gaussian-Lorentzian lines (CasaXPS software). The binding energy (BE), full width at half-maximum (FWHM) of the peaks and peaks area were determined from the fitting results. The carbon C is line at 284.8 eV was taken as a reference for surface-charging corrections.

Results

A. Catalytic Results

The synthesis of nitrogen-functionalized hydrocarbons through CO hydrogenation in the presence of ammonia is frequently reported at low pressure using a continuous stirred-tank reactor, for mainly technical reasons. Commercialized cylinders usually contain ammonia at pressures up to 10 bar. Under these conditions, ammonia is in a gas-liquid equilibrium. Running a high-pressure gas-phase reaction, such as the Fischer-Tropsch reaction, using liquid ammonia co-reactant, is straightforwardly conducted in a stirred-tank reactor. It is more challenging to perform the same reaction in a fixed-bed flow-reactor.

In the embodiments herein, high-pressure catalytic tests of CO hydrogenation in the presence of ammonia were performed in a fixed-bed flow reactor. Besides the aspect of mitigating ammonia corrosion, the ammonia phase diagram has to be carefully considered to ensure ammonia is being kept in the gas phase while feeding it into the reactor. To produce an ammonia gas feed of 20 bar, all gas lines from the cylinder to the reactor are heated to 55° C. The challenge is to make sure no gradient of temperature appears until the reactor entrance is reached. The benefit of using a fixed-bed reactor rather than a stirred slurry tank is the occurrence of less non-catalytic side reactions. For example, oxygenated hydrocarbons produced during the Fischer-Tropsch reaction could react with ammonia in the bulk slurry producing secondary products such as secondary or tertiary amines.

Exemplary oxygenates include alcohols and aldehydes. The examples of oxygenates further extend to, but are not limited to, mono-methyl and/or dimethyl linear alcohols and/or aldehydes and to derivatives of such molecules, such as alcohol ethoxylates, alcohol ether sulphonates, alcohol sulphates, alkyl glycerol ether sulphonates, alkyl poly glucosides, fatty alkanolamides, sulphomethyl esters, fatty acids, fatty esters and phthalates.

Catalysts were first investigated to determine their Fischer-Tropsch chain lengthening properties in the absence of ammonia. The data received was used as a reference for investigations in the presence of ammonia. Ammonia was introduced to the syngas feed once the Fischer Tropsch reaction was at steady state, which was reached after 24 h time on stream. Typically, catalytic tests were performed with an $H_2/CO$ ratio that varies from often 0.3 to 5, more often 0.3 to 0.4, and more often 0.3 to 5 wherein Nitriles are formed at a $H_2/CO$ ratio of about 0.3 to 0.5 and wherein Amines are formed at a $H_2/CO$ ratio between 2 up to 3, wherein the activating step includes performing the reaction in the presence of a promoter in order to generate $Co_2C$. Catalytic tests over this broad range of $H_2/CO$ ratios were never reported before for syngas/ammonia co-feeds. The rationale behind using broadly varying $H_2/CO$ ratios was to tune the selectivity of the reaction, so as to favor one class of functionalized hydrocarbons over the other in either presence or absence of ammonia in the feed gas. The total pressure was kept at 17 bar and the temperature at 260° C. in each catalytic test. Table 2 shows additional catalytic test results for $Co_4Mn_1K_{0.1}$. selectivity shown in the table do not include $CO_2$ production.

TABLE 2

| Catalytic tests result of the with on the CO hydrogenation on $Co_4Mn1Ko_{.1}$ | | | | | | |
|---|---|---|---|---|---|
| | $H_2/CO = 5$ | | $H_2/CO = 3$ | | $H_2/CO = 0.5$ | |
| | No $NH_3$ | $NH_3$ | No $NH_3$ | $NH_3$ | No $NH_3$ | $NH_3$ |
| % Alkanes | 89 | 67 | 35 | 39 | 23 | 26 |
| % Alkenes | 7 | 33 | 32 | 36 | 55 | 53 |
| % Alcohols | 4 | 0 | 33 | / | 7 | / |
| % Aldehyde | / | / | / | / | 15 | / |
| % Amines | / | / | / | 25 | / | 8 |
| % Nitriles | / | / | / | 0 | / | 13 |
| CO conversion | 87% | 81% | 56% | 31% | 19% | 11% |

According to Table 2, at over-stoichiometric $H_2/CO=5$ conditions, mainly alkanes (89%, ex-$CO_2$) are formed, with little to no alkenes appearing in the product spectrum. Adding ammonia drastically increases the selectivity of alkenes to 33% without forming nitrogen-functionalized products. The single-pass CO conversion (87%) in these experiments only slightly decreases in the presence of $NH_3$.

Adjusting the reactant feed to $H_2/CO=3$, in the absence of ammonia, causes the CO conversion to drop to 56% and to change the product spectrum to include alkenes (32%) and alcohols (33%), besides alkanes (35%). Remarkably, alcohols disappear in the presence of 15 vol % $NH_3$ and are replaced by aliphatic amines at a fraction of 25%, dominated by ethylamine. The CO conversion in these experiments drops to 31%.

Proceeding to under-stoichiometric FT conditions, $H_2/CO=0.5$, causes aldehydes to form (15%) while olefins increase (55%) and alkanes decrease (23%) as compared to measurements with higher $H_2/CO$ ratios. Aldehydes disappear quantitatively in the presence of $NH_3$ and are replaced by nitriles with a selectivity of 13%. CO conversion decreases from 19% in the absence of $NH_3$ to 11% in its presence. Remarkably, all experiments described here are completely reversible, i.e. the initial Fischer-Tropsch catalytic performance, whatever $H_2/CO$ ratio, is reproduced once ammonia is removed from the reactant feed.

Figure 4:
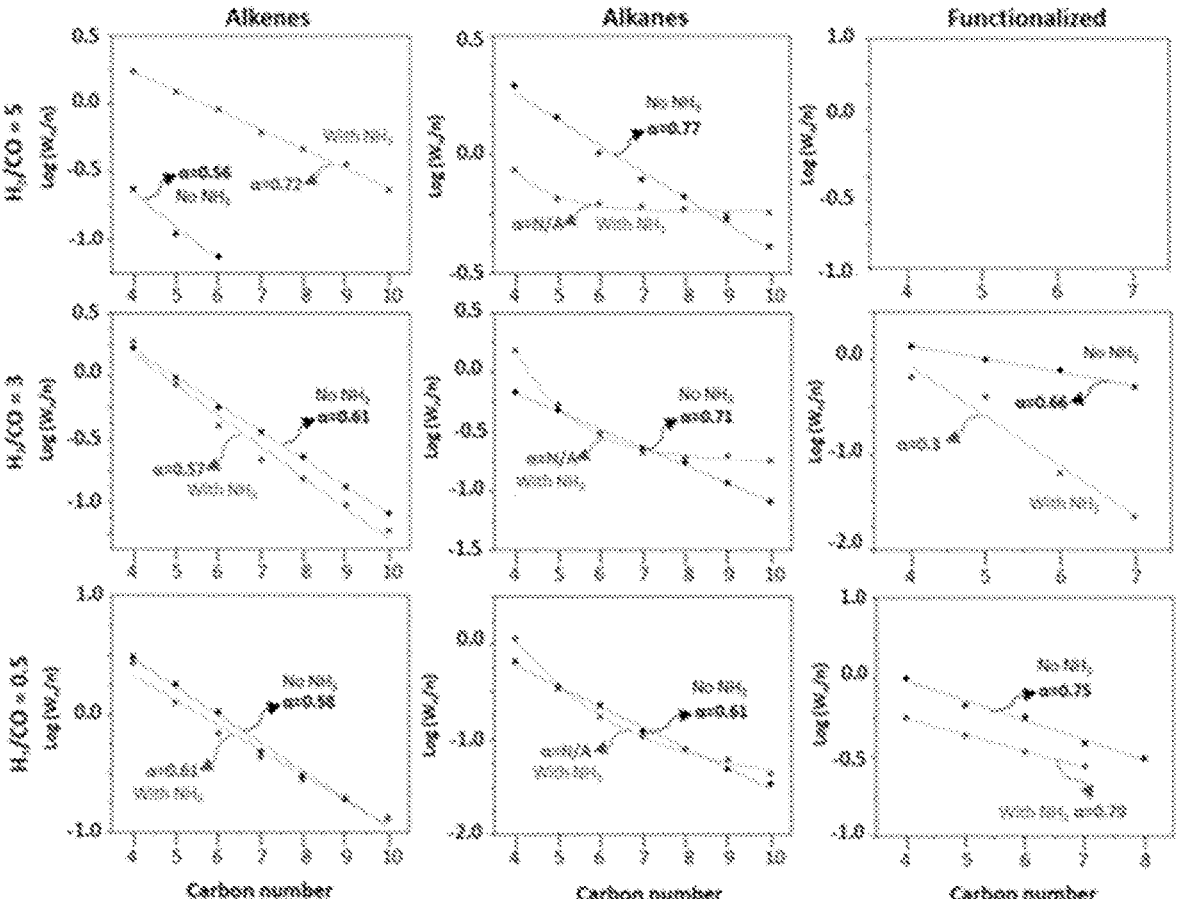
FIG. 4 shows Anderson-Schulz-Flory (ASF) chain-lengthening characteristics.

Product distributions have also been evaluated in terms of chain lengthening probabilities before and in the presence of ammonia. In particular, FIG. 4 plots show Anderson-Schulz-Flory (ASF) chain-lengthening characteristics. ASF plots of alkenes, alkanes and functionalized hydrocarbons (i.e. oxygenates before the addition of ammonia and nitrogen-containing products, such as amines and nitriles, after the addition of ammonia in the feed gas) of $Co_4Mn_1K_{0.1}$ compiled for different $H_2/CO$ ratios.

According to FIG. 4, Anderson-Schulz-Flory (ASF) plots show that, no matter the $H_2/CO$ ratio, ammonia drastically disturb the linearity of the alkanes $C_{4+}$ ASF. On the other hand, the chain lengthened of alkenes, nitrogen-containing compounds and oxygenates provide a linear $C_{4+}$ ASF dependence. At a ratio of $H_2/CO=5$, the chain growth probability of alkenes strongly increases in the additional presence of ammonia. Furthermore, the chain growth probability of nitrogen containing compounds ($\alpha=0.75$) is almost identical to the chain growth probability of oxygenates ($\alpha=0.79$). At $H_2/CO=3$ ratio, the chain growth probability of oxygenates ($\alpha=0.66$) drastically decreases in the presence of ammonia ($\alpha=0.30$). Ethylamine is mainly formed when ammonia is added to the feed gas at $H_2/CO=3$ ratio. The strongly non-linear $C_{4+}$ ASF dependence at this partial pressure ratio possibly indicates different chain growth mechanisms for short- and long-chain products. $C_1$-$C_3$ products are not shown in the ASF plots because they show major fluctuations and appear "disconnected" from the $C_{4+}$ product behavior.

Generally, results described herein were generally achieved by varying the $H_2/CO$ ratios to favor one class of functionalized hydrocarbons over others. Based on observations, it is frequently claimed that aliphatic amines or nitriles simply result from a gas phase reaction between alcohols or aldehydes with ammonia. This suspicion can be rejected for at least three reasons. First, alcohols disappear as soon as ammonia is introduced in the feed gas. N-containing hydrocarbon products are, however, only formed once $Co_2C$ has been generated due to a reaction-induced reconstruction of the catalyst which can take hours under atmospheric reaction conditions. It took about 8 hours after introducing ammonia to the feed gas to start observing N-containing compound in the gas phase. This observation strongly suggests that the surface of the catalyst had to be restructured in order to form the precursors that are responsible of the synthesis of N-containing compounds.

Second, if this claim were accurate, N-containing compounds and oxygenates would both have appeared in the gas phase concomitantly reaching a reaction equilibrium after a certain amount of time, this was not observed. Instead, alcohols instantaneously disappeared when ammonia was introduced in the feed stream. Moreover, the gas phase reaction between an oxygenate and ammonia should not modify the ASF chain lengthening behavior. Alcohols and aldehydes yet were detected up to $C_{10}$ while amines and nitriles were detected up to $C_7$, with short-chain nitrogen-compounds such as ethylamine being dominating. This indicates that chain lengthened amines and nitriles result from a polymerization reaction that occurs on the surface of the catalyst.

Finally, yet importantly, those of ordinary skill in the art have noted that at these experimental conditions, the gas-phase amination of alcohols occurs and secondary amines are produced. Secondary amines were not detected here since amines/nitriles and alcohols/aldehydes did not appear simultaneously in the gas phase. They have rather to be considered products formed in surface reactions with variable chemical composition of the most abundant surface reaction intermediates ("mari"). CO insertion into either N—H(R) or O—H(R) target bonds of "mari" species initiate and maintain the growth of hydrocarbon scaffolds. Elimination steps with either ammonia or water rejection are thought to be responsible for the high yields of chain-lengthened alkenes.

B. Catalyst Characterization

Figure 5:
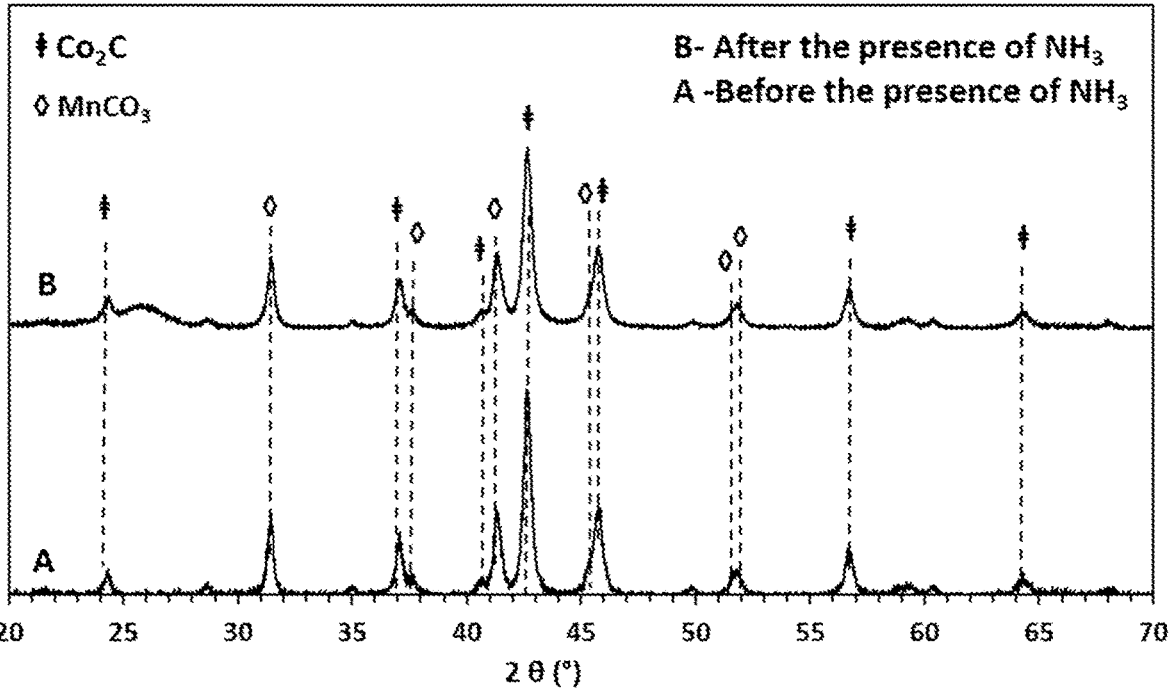
FIG. 5 shows the XRD patterns of $Co_4Mn_1K_{0.1}$ before and after the exposure to ammonia.

XRD analysis was performed after 100 h time on stream. The diffraction lines centered at $2\theta$ of 37.1, 41.4, 42.7 and 45.8° before the introduction of ammonia in the feed gas (see FIG. 5) correspond to the (110), (002), (111) and (021) planes of $Co_2C$. No change in these diffraction patterns is encountered when ammonia is present in the gas feed. Note that the peak at $2\theta$~44.3° may also be attributed to hcp cobalt. $MnO_x$ phases were not observed in the XRD pattern, possibly due to their poor crystallinity and/or small aggregate size. Peaks at 31.5°, 37.7°, 41.6°, 45.3°, 49.9°, 51.7° and 51.8° correspond to $MnCO_3$.

C. Surface Analysis

Figure 6:
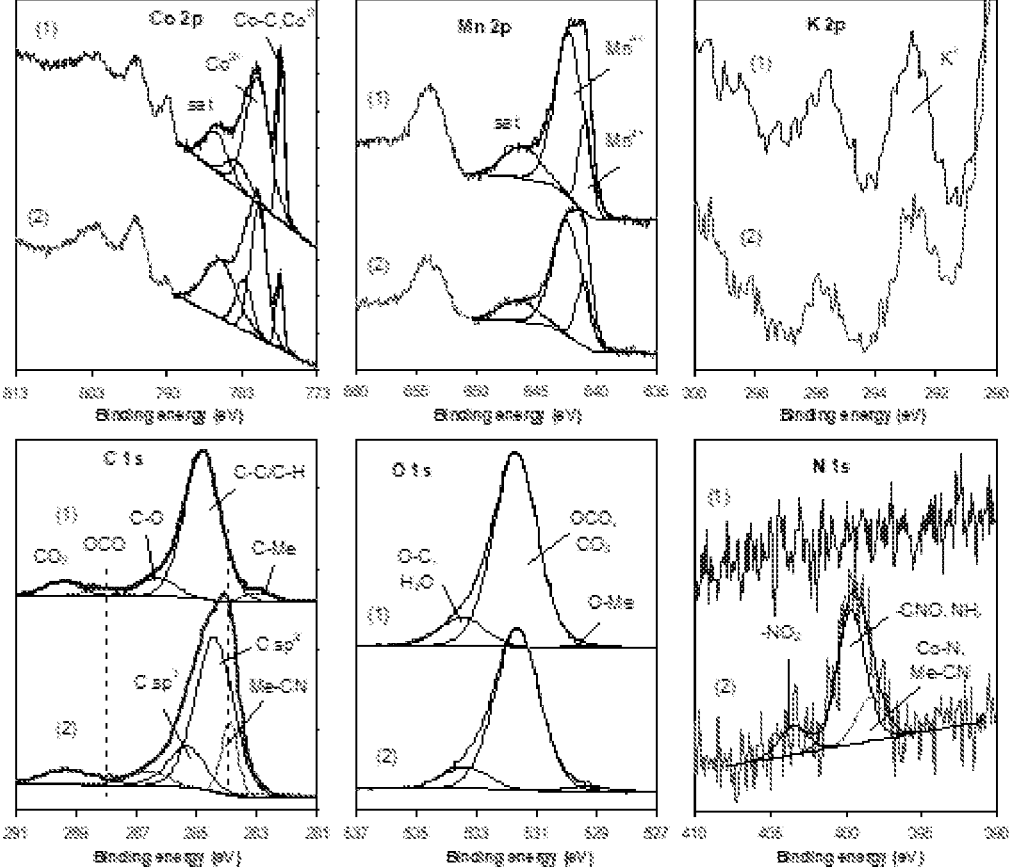
FIG. 6 shows the curve-fitted Co 2p, Mn 2p, K 2p, C 1s, O 1s and N 1s core-level XP spectra for Co4Mn1K0.1 catalyst after usual CO hydrogenation (1) and after CO hydrogenation in the presence of $NH_3$ (2). Chemical species derived from deconvolution of the spectra are indicated.

FIG. 6 shows the survey spectra of the catalyst used in reactions 1 (in the absence of $NH_3$) and 2 (in the presence of ammonia). Note that hereafter referred to as sample-1 and sample-2, respectively. Sample-1 reveals the presence of Co, Mn, K, C and O. In sample-2, in addition, a pronounced peak of nitrogen is detected. The high-resolution Co 2p, Mn 2p, K 2p, C 1s, N 1s and O 1s core-level spectra of both samples are presented in FIG. 6. By using areas under the peaks and standard sensitivity factors, the surface composition of the samples was evaluated.

FIG. 6 provides the curve-fitted Co 2p, Mn 2p, K 2p, C 1s, O 1s and N 1s core-level XP spectra for $Co_4Mn_1K_{0.1}$ catalyst after usual CO hydrogenation (1) and after CO hydrogenation in the presence of $NH_3$ (2). Chemical species derived from deconvolution of the spectra are indicated.

As can be seen in FIG. 6, cobalt is in two chemical states. The pronounced intense Co 2p3/2 peak at 777.9 eV with a spin-orbit splitting (SOS) of 15.1 eV corresponds to metallic Co(0). The existence of metallic cobalt in the spent catalyst exposed to air can be explained by the formation of a protective superficial layer of catalytically produced carbon the surface concentration of which is rather high. The broad Co 2p3/2 component at 780.9 eV accompanied by a multiplet splitting component and a satellite at 786.5 eV indicates unambiguously the $Co^{2+}$ chemical state. Manganese appears to be also in two chemical states. A distinct Mn 2p3/2 component at BE=640.9 eV accompanied by a satellite at 646.1 eV can be assigned to $Mn^{2+}$ oxidation state, whereas the component at 642.2 eV corresponds to Mn4+ state (FIG. 6). The broad component at 642.2 eV, however, may be composed of a mixture of unresolved $Mn^{3+}$ and $Mn^{4+}$ states. These chemical states imply the catalyst surface to be covered with a mixture of CoO (or/and Co(OH)2), MnO and MnO2 which can form a spinel-like oxide (Co,Mn)Ox. Note that the total atomic ratio $O/(Co^{2+}+Mn^{2+,4+})=4.2$. The K 2p3/2 peak at 292.8 eV (FIG. 6) indicates the potassium to be in the ionized state K+ (like in $K_2O$). The C is spectrum can be decomposed into 5 components (FIG. 6). A pronounced low-BE component at 282.9 eV indicates unequivocally the formation of a Me-C carbide. This C 1s carbidic component implies that the Co 2p3/2 component at 777.9 eV is also related to Co—C bonds since the binding energies of the Co 2p3/2 peak in pure metallic cobalt and cobalt carbides are practically indistinguishable. The dominant component in the C is band at 284.8 eV corresponds to C—C/C—H bonding in the surface disordered carbonaceous layer. There are also three more minor components at 286.3, 288.1 and 289.5 eV which can be attributed to C—O, O—C=O and —$CO_3$ species, respectively. In the O 1s spectrum (FIG. 6), the components at 529.4, 531.6 and 533.3 eV can be related to O-Me bonds, OH—/OCO/$CO_3$ species and O—C/$H_2O$ads species, respectively. The carboxyl-type C is component at 288.1 eV separated from the respective O 1s component by a characteristic value of 243.5 eV can be identified as a formate-like species. Formate is supposed to grow during the course of reaction on the $Co_2C$ surface or at the interface between $Co_2C$ and (CoMn)—Ox. Also, a distinct C is component at 289.5 eV and its energy separation from the respective O 1s component ΔBE (O1s-C1s)= 242.1 eV, which is a characteristic value for carbonates, unambiguously indicate the presence of a carbonate on the sample-1 surface. The $Mn^{2+}$ component in the Mn 2p spectrum (FIG. 6) with a SOS of 11.9 eV and unusually intense satellite implies a significant contribution of $MnCO_3$ to this peak. Finally, the N is spectrum of sample-1 (FIG. 6) shows traces, if any, of —$NO_2$ species adsorbed from air on the catalyst surface. After reaction in the presence of ammonia, an appreciable N is peak is detected on the sample-2 surface (FIG. 6) which evidences adsorption and dissociation of $NH_3$ on the catalyst surface. The addition of $NH_3$ to the feed gas mixture causes a strong modification of the surface chemical state of the spent catalyst. The formation of cobalt carbide decreases. Instead, adsorption and dissociation of $NH_3$ on the catalyst surface give rise to the formation of cobalt nitride, oxynitride and/or cobalt cyanide, oxycyanide-like bonds (Co—N, O—Co—N, Co—CN, Co—CN—O). In the presence of $NH_3$, a larger amount of amorphous carbon is deposited on the catalyst surface than under pure FTS conditions. Besides, probably due to enhanced hydrogenation in this case, carbon deposits in two different hybrid forms as graphite-like sp2 and diamond-like sp3 carbon with sp3/sp2=0.24. Besides, with $NH_3$ in the feed gas, the content of oxygenated carbon species (C—O bonds) decreases, the carbonate appears to be oxygen-deficient and no carboxyl-type species forms.

The surface chemical composition in the absence of ammonia is made up of 3.95% Co, 2.5% Mn, 0.45% K, 69% C and 23.9% O. The surface concentration changes of 2.8% Co, 1.39% Mn, 0.2% K, 0.57% N, 79.6% C and 15.4% O for feeds containing ammonia. Thus, XPS analysis shows that there is less oxygen on the surface when ammonia is present in the feed gas, which concords with CTK results. Besides, another small C is component at BE=288.2 eV (characteristic of OCO bonding) as well as the difference in BEs (O1s-C1s) for this component=243.5 eV which formally corresponds to formate. Interestingly, such formate component is only observed for feeds free of ammonia, which means that ammonia inhibits the formation of formate considered to be most abundant surface intermediates in the Fischer-Tropsch reaction to chain-lengthened oxygenates.

Example 3

Experimental Procedure/CTK Principle Details

Prior to CTK studies, oxalate precursors were thermally decomposed and activated in situ under 10 mL of hydrogen and 20 mL of argon for 1 hour at 390° C. The CTK experiments were performed at 220° C. and at atmospheric pressure and consisted in triggering sudden changes of the reactant feed composition to follow either the construction of the catalytically active phase or its scavenging as a function of time. After careful calibration, rates of reactant consumption and product formation (in molecules/seconds) were calculated at any time during the transient periods.

Generally, the procedure of the CTK studies comprised the exposure of the catalyst to a non-reactive gas mixture ($H_2$/Ar) until the dynamic adsorption/desorption equilibrium of $H_2$ was reached. Next, this non-reactive feed gas was swiftly replaced by a reactive feed gas consisting of a mixture of $H_2$/CO/$NH_3$/He. Usually the $H_2$ inlet flow and the total flow rate were kept constant during the switch. The switch from non-reactive to reactive gas mixtures was coined "build-up of the reaction". The last step of the CTK study comprised switching back to non-reactive feed gas thereby triggering the scavenging stage or "back-transient of the reaction". The gases leaving the reactor were continuously analyzed by a quadrupole MS and GC-MS (Agilent 7890A GC/5975 MS) during the entire CTK study.

Chemical Transient Kinetics Studies

1) Build-Up of the Catalytically Active Phase

Figure 8:
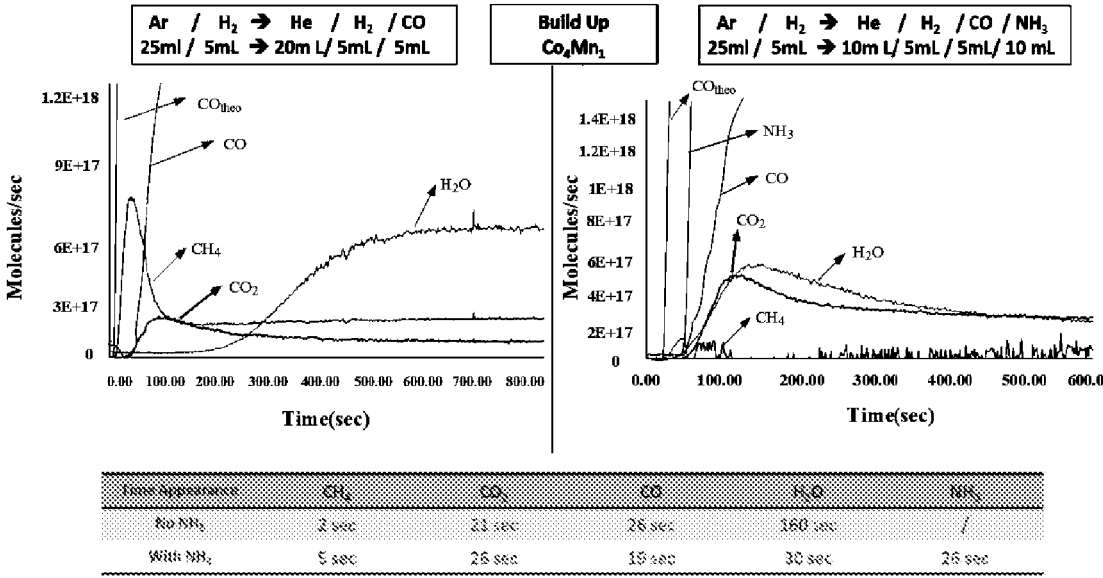
FIG. 8 shows build-ups generated over $Co_4Mn_1$ catalysts.

FIG. 8 shows the outlet flows for an unpromoted $Co_4Mn_1O_x$ catalyst during the buildup of the catalytically active phase of the reaction. The build-up is triggered by two different gas mixtures, one containing ammonia and the other not. Note that both build-ups are performed with fresh catalysts from the same batch preparation. Very similar build-up results are obtained with $Co_4ZrO_x$ (FIG. 9).

Figure 7:
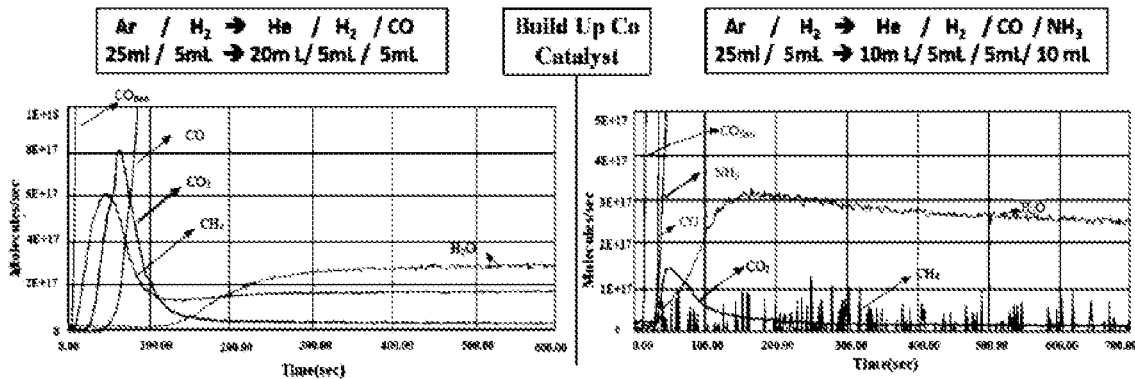
FIG. 7 shows build-ups generated over bare cobalt catalyst.
Figures 9, 10:
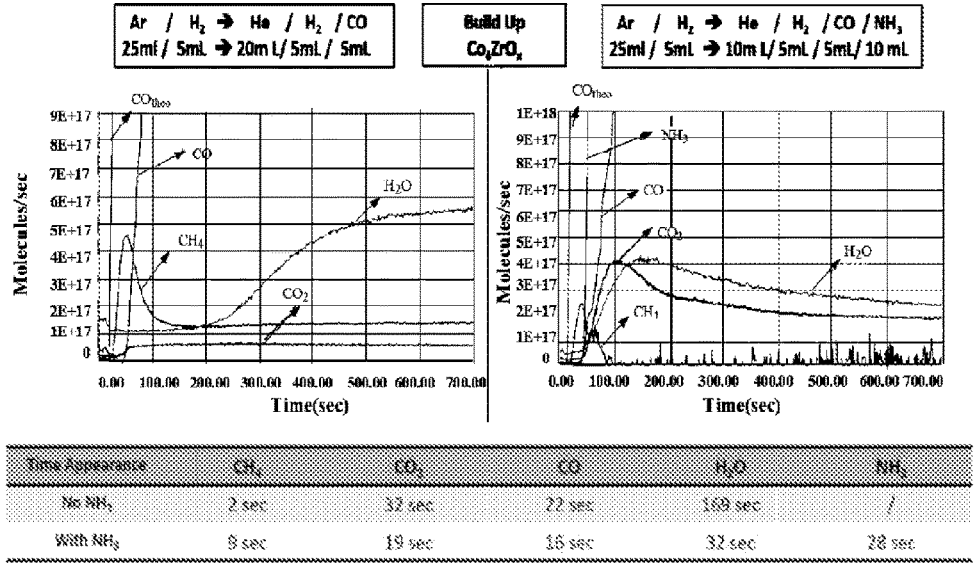
FIG. 9 shows build-ups generated over $Co_4ZrO_x$ catalysts.
FIG. 10 show GC-MS results of each steady state of the build-ups investigated.

FIGS. 7, 8 and 9 allow each species to be associated with a characteristic time of appearance, i.e. a delay time relative to the helium flow (corresponding to the flow of CO in case it would not undergo chemisorption). In any case, the first species appearing in the gas phase during the build-up is methane demonstrating that the CO molecule dissociates fast into carbon and oxygen. However, much less methane is formed when ammonia is used as a co-reactant in the gas mixture. Ammonia is actually strongly inhibiting methane formation. CO appears in the gas phase when methane production reaches a maximum. $CO_2$ seems to appear somewhat earlier than CO while the reverse is true for gas mixtures comprising ammonia reactant. Remarkably, water product is largely delayed in the absence of ammonia and much less so in its presence. Last but not least, the "breakthrough" appearance time of ammonia is rather long (even longer than for CO). It has been observed that this delay time increases with the acidity of the metal oxide promoters. This influence is interpreted as being caused by variations of the binding energy of adsorbed ammonia at sites of different Bronsted/Lewis acidity. Generally, the time dependent features of reactant breakthrough and basic product formation are the consequence of rearrangement processes at the catalyst surface leading to most abundant reactive intermediates ("mari") and the formation of chain-lengthened products. The latter have been omitted in FIGS. 7, 8 and 9 for the sake of clarity, but compiled in FIG. 10 for steady-state conditions after build-up.

The steady-state after build-up was analyzed by GC-MS in order to have a quantitative analysis of the outlet flows. The results are shown in FIG. 10 and demonstrate, despite a lower CO conversion, gas mixtures containing ammonia lead to a higher selectivity toward olefins and a strong inhibition of methane formation. On the other hand, the selectivity of $CO_2$ formation can be undesirably high when using metal oxide promoters. It has been observed, however, that the $CO_2$ formation can be largely suppressed in model experiments at atmospheric pressures using Co catalysts in the absence of metal oxides.

Figure 11:
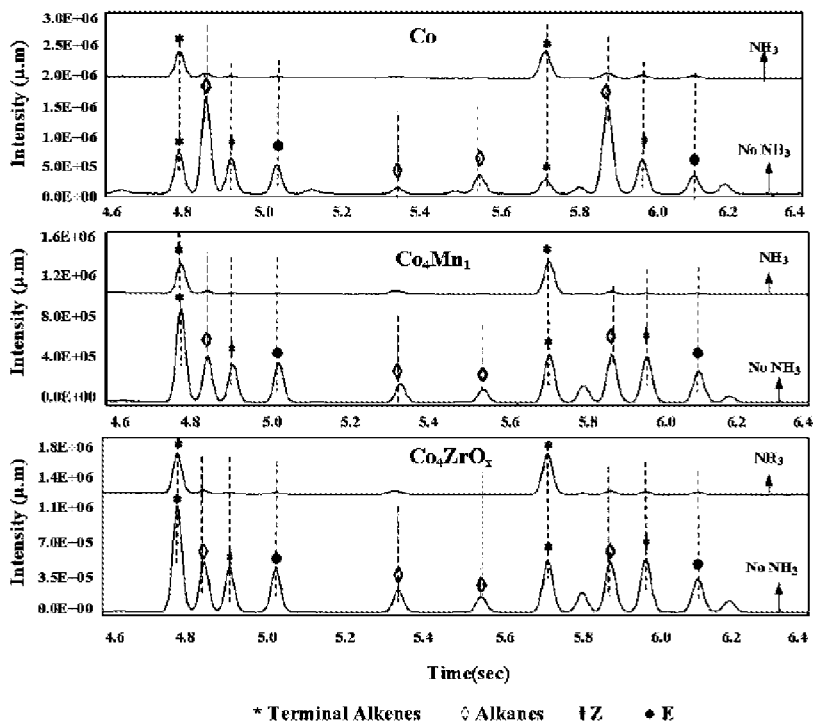
FIG. 11 shows region of the chromatograms obtained during the steady-state of the build-ups.

FIG. 11 shows a region of the GC-MS chromatogram for a typical build-up study before steady-state is reached. It is clearly seen that the presence of ammonia inhibits the formation alkanes (both straight ones and isomers Z/E) while that of olefins is favored, which suggests that alkanes and isomers follow a different synthesis pathway than olefins. The results also show that nitriles are formed when the feed gas contains ammonia. No oxygenates, such as alcohols or aldehydes, are detected under these conditions. The suppression of alkane formation and preference of olefin formation is actually being observed to be rather independent of the catalyst composition and applies even to bare Co metal in the absence of any support. Product distributions have also been evaluated in terms of chain lengthening probabilities for steady-states after build-up. Anderson-Schulz-Flory (ASF) plots show that ammonia drastically disturbs the ASF linearity of $C_{4+}$ alkanes. No such behavior is seen for alkenes, i.e. a linear ASF dependence is obtained instead.

Figure 12:
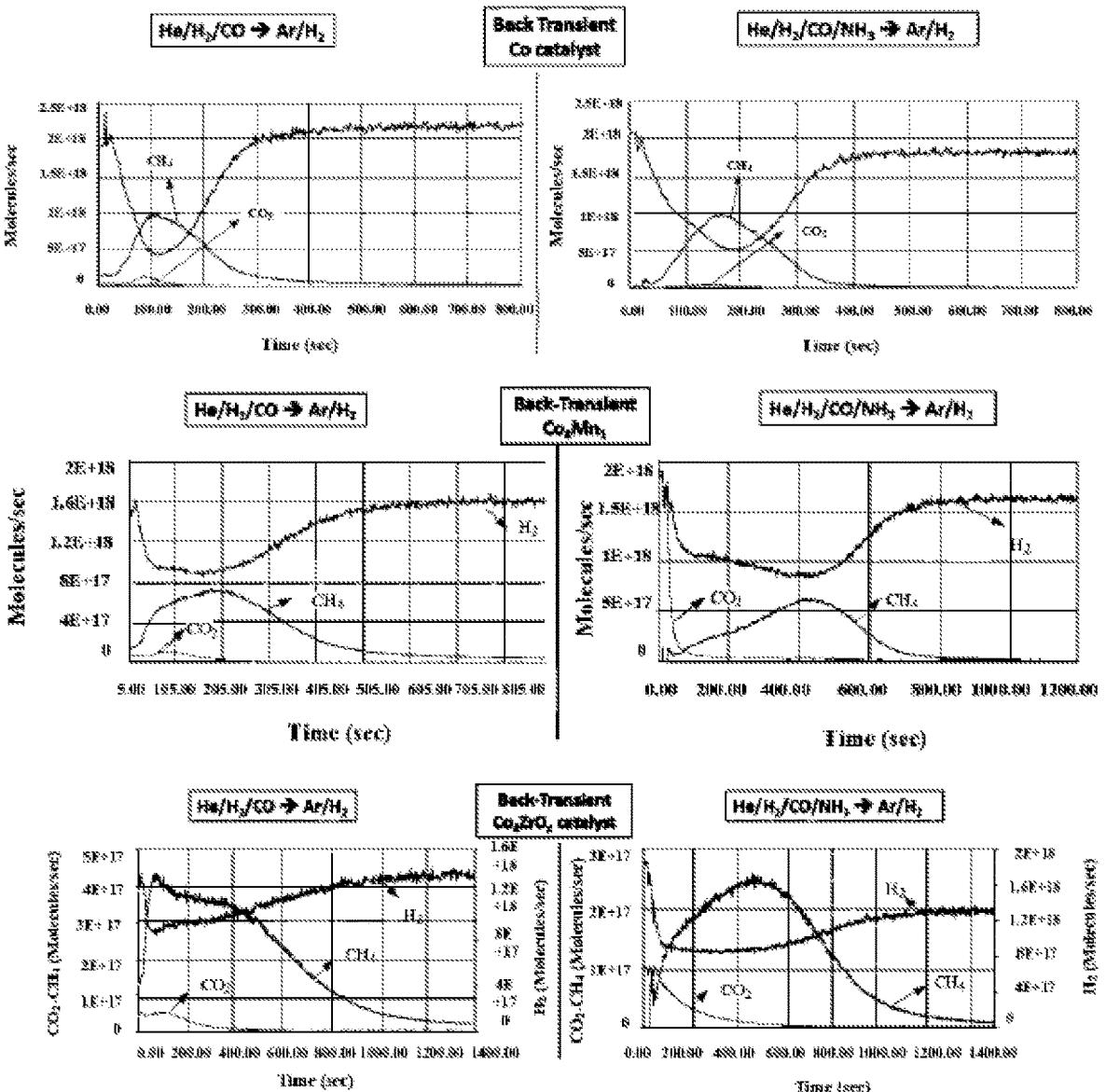
FIG. 12 shows back-transient of catalysts investigated.

FIG. 12 shows the outlet flows during back-transients. Hydrogen is consumed during the back-transients while methane is being transiently produced. This behavior has been observed for all Co-based catalysts, including bare Co metal. The significant amount of methane detected during back transients is associated with the reduction of $Co_2C$ to metallic Co. Some $CO_2$ also appears during back transients. Interestingly, such $CO_2$ is mainly formed over bare Co catalysts suggesting that carbonate structures formed during synthesis on metal oxide promoters are being decomposed during back-transients.

Accordingly, the characterization of the catalyst by XRD and XPS shows that cobalt carbide, which has never been reported for the CO hydrogenation in the presence of ammonia, was present before and after the addition of ammonia in the feed gas. $Co_2C$ has been demonstrated to be active key catalyst phase responsible for forming oxygenates.

Following this reasoning, $Co_2C$ is also deemed to be a prerequisite for forming nitrogen-containing compounds. The reversibility of the catalytic tests is in line with the assumption that the bulk of the catalyst, $Co_2C$, is not reduced by ammonia but, instead, allows its adsorption and formation of surface amine complexes. It is hypothesized that CO insertion into the N—H bond of adsorbed amine initiates the chain growth. This step is similar to the mechanism of oxygenate formation, in the absence of ammonia, where a CO insertion step into the O—H bond of adsorbed hydroxyl is deemed to be key to chain growth. XPS analyses support the idea that chain-lengthened amines and nitriles result from a polymerization occurring at the surface of the catalyst.

Catalysts for amine and nitrile synthesis clearly show cobalt particles to be transformed into $Co_2C$, similar to observations for the FT synthesis leading to alcohols and aldehydes. Atmospheric CTK studies demonstrate that alkanes and alkenes appear in order of mention when swiftly switching from $H_2$ adsorption to $H_2/CO$ reactive conditions (oxygenates are not formed here, for thermodynamic reasons). Then, when switching from $H_2/CO$ to $H_2/CO/NH_3$ feeds, a drastic increase of alkenes at the expense of alkanes is observed. Therefore, alkenes cannot be considered precursors of alkanes, especially at short reaction times during transients where the formation kinetics dominate.

Although one aspect of the present invention is to synthesize aliphatic amines and nitriles, the amines and nitrile products may further be reacted to form amides or formamides by supplying additional precursors to be used in a plurality of reactions known in the art (e.g., acyl chloride based reaction).

It is to be understood that features described with regard to the various embodiments herein may be mixed and matched in any combination without departing from the spirit and scope of the invention. Although different selected embodiments have been illustrated and described in detail, it is to be appreciated that they are exemplary, and that a variety of substitutions and alterations are possible without departing from the spirit and scope of the present invention.

The invention claimed is:

1. A reactor-based hydrogenation process for producing nitrogen containing hydrocarbons, comprising activating one or more cobalt-based catalysts with a synthesis gas comprising carbon monoxide (CO) and hydrogen ($H_2$) to form $Co_2C$ on one or more activated cobalt-based catalysts;

reacting the CO and $H_2$ under Fischer-Tropsch reaction conditions in a presence of ammonia and the one or more activated cobalt-based catalysts to produce at least one aliphatic amine and/or nitrile, and during reacting, controlling a ratio of the $H_2$ to the CO to 0.3:1 to 7:1 to selectively form the at least one aliphatic amine and/or nitrile.

2. The process according to claim 1, wherein the reaction is performed in a fixed bed reactor at a reaction temperature of between 180° C. to 300° C.

3. The process according to claim 1, wherein the reaction is performed at a pressure between 1 to 25 bar.

4. The process according to claim 1, wherein the ratio of the $H_2$ to the CO is adjusted from an initial ratio to the controlled ratio of 0.3:1 to 7:1 after the one or more cobalt-based catalysts are activated.

5. The process according to claim 1, wherein the ratio of the $H_2$ to the CO is controlled at to 0.3:1 to 0.5:1 for selectively producing nitriles over other nitrogen containing compounds.

6. The process according to claim 1, wherein the ratio of the $H_2$ to the CO is controlled at 2:1 to 3:1 for selectively producing amines over other nitrogen containing compounds.

7. The process according to claim 1, wherein the reacting is performed in a fixed bed reactor, and wherein the ratio of the $H_2$ to the CO is set to a first ratio of 0.3:1 to 0.5:1 for selectively producing nitriles in the fixed bed reactor and is subsequently adjusted to a second ratio of 2:1 to 3:1 for selectively producing amines in the fixed bed reactor.

8. The process according to claim 7, wherein the step of activating the one or more cobalt-based catalysts is performed in the fixed bed reactor when the ratio is set to the first ratio for a sufficient amount of time.

9. The process according to claim 8, wherein the sufficient amount of time is 20-30 hours.

10. The process according to claim 1, wherein the one or more cobalt-based catalysts include a combination of a dispersant promoter selected from an oxide or a metal of Mn, Ti, Mg, Cr, Ca, Si, Al, Zn, Cu or combinations thereof, and a promoter for influencing product selectivity selected from an alkali oxide, K, Li, Na, Cs or combinations thereof.

11. The process according to claim 1, wherein the one or more cobalt-based catalysts are precipitated, sintered, impregnated or dispersed onto a support, wherein the support is selected from an oxide of Ti, Mn, Si, Al or combinations thereof.

12. The process according to claim 1, wherein the one or more cobalt-based catalysts comprise $Co_xMn_yK_z$, wherein x is 2-4, y is 1-5 and z is 0.1-0.3.

13. The process according to claim 12, wherein the $Co_xMn_yK_z$ is synthesized via oxalate precipitation to form $Co_4Mn_1K_{0.1}$.

14. The process according to claim 1, further comprising removing ammonia from the synthesis gas after the reacting step.

15. The process according to claim 1, wherein the at least one aliphatic amine or nitrile is at a terminal position of the nitrogen containing hydrocarbons.

16. The process according to claim 1, wherein the at least one aliphatic amine or nitrile is not produced by a non-catalyzed reaction of ammonia and oxygenates in a gas phase.

17. The process according to claim 16, wherein the oxygenates are alcohols, aldehydes and carboxylic acids.

18. A method to catalytically synthesize chain-lengthened hydrocarbons with terminal nitrogen functionalization, comprising:

activating a cobalt-based catalyst with a feed gas, wherein the feed gas comprises carbon monoxide (CO) and hydrogen ($H_2$), and the activation forms $Co_2C$ on the cobalt-based catalyst, wherein the activating step includes performing a reaction at a first $H_2/CO$ ratio of 0.3:1 up to 0.5:1 for at least 24 hours in a presence of a promoter in order to generate the $Co_2C$;

providing a temperature between 180° C. and 300° C. under a pressure between 1 bar to 25 bar in a reaction vessel containing the activated cobalt based-catalyst; and combining ammonia with the CO and the $H_2$ in the reaction vessel and reacting the CO and the $H_2$ to produce nitrogen-containing compounds which comprises at least one aliphatic amine and/or nitrile.

19. The method of claim 18, wherein the activated catalyst is synthesized via oxalate precursors.

20. The method of claim 18, wherein the activated catalyst includes at least one Mn-oxide or Zr-oxide-promoting transition metal or rare-earth metal.

21. The method of claim 18, wherein the activated catalyst is further promoted by alkali.

22. The method of claim 18, in which the formation of oxygenates such as alcohols and aldehydes is suppressed.

23. The method of claim 18, wherein the formation of alkanes and iso products is inhibited.

24. The method of claim 18, wherein the formation of methane is inhibited.

25. The method of claim 18, wherein the ratio of hydrogen to carbon monoxide is varied from 0.5:1 to 7:1.

26. The method of claim 18, wherein the step is performed at a second $H_2/CO$ ratio between 2:1 up to 3:1 to selectively form amines, or the first $H_2/CO$ ratio of about 0.3:1 to 0.5: to selectively form nitriles.

* * * * *